United States Patent [19]

Frengen

[11] Patent Number: 5,723,346
[45] Date of Patent: Mar. 3, 1998

[54] METHOD OF ASSAY USING TWO DISTINGUISHABLE TYPES OF PARTICLES

[75] Inventor: Jomar Frengen, Trondheim, Norway

[73] Assignee: Sinvent AS, Trondheim, Norway

[21] Appl. No.: 663,122

[22] PCT Filed: Dec. 23, 1994

[86] PCT No.: PCT/GB94/02816

§ 371 Date: Oct. 1, 1996

§ 102(e) Date: Oct. 1, 1996

[87] PCT Pub. No.: WO95/17674

PCT Pub. Date: Jun. 29, 1995

[30] Foreign Application Priority Data

Dec. 23, 1993 [GB] United Kingdom .................. 9326379

[51] Int. Cl.⁶ .................................................. G01N 33/543
[52] U.S. Cl. ...................... 436/523; 435/7.93; 435/7.94; 435/962; 435/973; 435/975; 436/501; 436/518; 436/524; 436/525; 436/528; 436/531; 436/534; 436/805; 436/808
[58] Field of Search .................... 435/7.93, 7.94, 435/962, 973, 975; 436/501, 518, 523, 524, 525, 526, 528, 531, 534, 805, 808

[56] References Cited

U.S. PATENT DOCUMENTS 4,743,542  5/1988  Graham et al. .
5,369,036  11/1994  Mercolino et al. ................. 436/523

FOREIGN PATENT DOCUMENTS 0 038 181  10/1981  European Pat. Off. .
0 194 156  9/1986  European Pat. Off. .
0 263 731  4/1988  European Pat. Off. .
89/11101  11/1989  WIPO .

OTHER PUBLICATIONS

Frengen et al., "A sequential binding assay with a working range extending beyond seven orders of magnitude," *Journal of Immunological Methods*, vol. 178, No. 1, pp. 131–140, (1995).

Frengen et al., "Dual analyte assay based on particle types of different size measured by flow cytometry," *Journal of Immunological Methods*, vol. 178, No. 1, pp. 141–151, (1995).

Utgaard et al., "Analyte and label binding assay read by flow cytometry," *Clinical Chemistry*, vol. 42, No. 10, pp. 1702–1708, (1996).

*Primary Examiner*—Susan Wolski
*Attorney, Agent, or Firm*—Bacon & Thomas

[57] ABSTRACT

The present invention relates to a binary assay method capable of providing wide dynamic range and a high degree of precision in which analyte and labelled ligand are reacted with two independently determinable forms of solid-supported binding partners having affinity for the analyte and labelled ligand, respectively. The analyte concentration is determined from signals deriving from the resulting two forms by reference to a double standard calibration curve. A kit for use in the method is also disclosed.

14 Claims, 2 Drawing Sheets

METHOD OF ASSAY USING TWO DISTINGUISHABLE TYPES OF PARTICLES

This application was filed under 35 U.S.C. §371 as the national stage of International Application PCT/GB94/02816, filed Dec. 23, 1994.

This invention relates to a method of assaying an analyte and to kits useful in such a method.

Assay techniques for determining the presence and desirably also the concentration of an analyte using a binding partner having specificity for that analyte are frequently encountered, e.g. in the fields of biochemistry and clinical chemistry. Thus, for example, a wide range of immunological and related techniques has been proposed for determining materials such as antigens in serum, using an appropriate binding partner for the analyte, such as a specific antibody (e.g. a monoclonal antibody) for a particular antigen.

One such technique comprises competitive binding assays, in which a known amount of a labelled version of an analyte to be determined (e.g. carrying a radioactive label) and a relatively small known amount of a binding partner therefor are incubated with the analyte to be determined, whereby the labelled and the naturally-occurring analyte compete for the binding partner. The amount of labelled analyte bound to the binding partner is thereafter determined and the concentration of the naturally-occurring analyte, which will bear an inverse relationship to this amount, is assessed from a previously established standard curve.

Another useful technique comprises sandwich assays. These employ an excess of binding partner, the analyte which binds thereto being labelled by treatment with a labelled ligand also having affinity for the analyte. The amount of bound and labelled analyte is then determined and permits the analyte concentration to be assessed by reference to a standard calibration curve.

The binding partner and the labelled ligand in such sandwich assays preferably have affinities for different binding sites (e.g. epitopes) on the analyte. The ligand may, for example, be labelled for reading on the basis of radioactivity, light absorption or fluorescence.

Sandwich assays tend to exhibit greater sensitivity than competitive binding assays and are therefore usually preferred. It will be appreciated that high sensitivity is essential in, for example, immunoassays in clinical laboratories, where it may be required to quantify e.g. antigens present in serum at concentrations in the nmol/l to pmol/l range or even lower.

The binding partner in both the above-described types of assay is commonly coupled to a solid support in order to facilitate isolation of the bound analyte and competing or analyte-bound label. Thus, for example, the binding partner may be coupled to the surface of a reaction vessel, e.g. to the surfaces of the wells of a microtiter plate made from a suitable plastics material, so as to facilitate washing to remove unbound excess labelled ligand.

Alternatively the binding partner may be coupled to the surfaces of an array of particles, for example made of a suitable plastics material such as polystyrene or polyacrylate. Separation of the bound analyte/label from free label may then be effected by, for example, filtration or, in the event that superparamagnetic particles are employed, by application of a magnetic field. The particles are advantageously of microscopic size in order to present a large total surface area coated with the binding partner. The use of monosized microparticles is preferred since it ensures that the particles exhibit standard binding properties.

A disadvantage of the above-described basic assay techniques is that separation of the bound analyte and label and associated washing steps to remove unbound label are inherently time-consuming and labour-intensive. It is known, however, that this problem may in principle be avoided in the case of particle-based assays if the particles are analysed by means of flow cytometry. This typically involves passage of a suspension of particles through the measurement region of a photometer in such a way that successive individual particles are irradiated with excitation light, causing emission of a pulse of scattered light related to the size of the particle and a further signal, e.g. a pulse of fluorescent light, related to the amount and nature of the label bound to the particle. Suitable electronic detectors and microprocessors classify and store the results, whereby measurements in respect of $10^4$–$10^5$ individual particles may readily be obtained in e.g. one minute of data acquisition time. Hydrodynamic focusing of the sample stream in a flow cytometer results in the measurement region (i.e. the volume of sample stream within the excitation/detection region) being very small, typically of the order of $(10 \ \mu m)^3$, so that the amount of unbound label present in the liquid surrounding an individual particle being measured will be insignificant. Accordingly there is no need to separate unbound label prior to the flow cytometric particle analysis, which is therefore said to be a homogeneous, i.e. separation free, assay.

A general problem associated with sandwich assays in particular, including those performed using flow cytometric techniques, is that their dynamic range is limited by a phenomenon known as the hook effect, which occurs at high analyte concentrations. Thus the binding partner is normally used in a fixed amount, the theoretical maximum detectable analyte concentration thus being determined by the total available binding capacity of the binding partner for the analyte. Since, however, the labelled ligand is also normally used in a fixed amount, the amount of label available per bound analyte molecule will effectively decrease when the analyte concentration exceeds this theoretical maximum, as a result of increasing binding of the label to excess unbound analyte remaining in solution. In other words, the unbound excess analyte competes with the bound analyte for the label and thereby reduces the amount of label immobilised on the bound analyte. This will lead to a decrease in the observed level of bound analyte/label as the analyte concentration increases above the level at which the binding partner becomes saturated. Accordingly, calibration curves of signal intensity in respect of bound label against analyte concentration rise to a maximum and then fall off as the analyte concentration increases further, with the result that signal intensities cannot unambiguously be ascribed to a single concentration value unless additional steps, e.g. involving dilution of the sample and further assaying, are carried out.

Whilst the onset of the hook effect can in principle be delayed by increasing the amount of binding partner used this will inevitably lead to reduced sensitivity at low analyte concentrations, since measurement techniques such as flow cytometry require a certain minimum level of bound analyte/label per particle to give accurately detectable results.

U.S. Pat. No. 4,595,661 suggests that the hook effect in an immunoassay may be reduced by using an additional antibody, which may optionally be labelled and/or bound to a solid carrier, and which has a lower affinity for the target antigen than the primary binding partner antibody and labelled ligand. Although this low affinity antibody may delay onset of the hook effect by binding with the analyte at high analyte concentrations, its presence will again reduce the sensitivity of the assay at low analyte concentrations as a result of increased background interference, non-specific binding etc.

A similar approach is described in U.S. Pat. No. 4743542, where the principle is again to add unlabelled antibody in competition with the labelled ligand in an immunoassay. By acting as an additional reagent for the antigen, this unlabelled antibody raises the antigen concentration at which saturation of the primary binding partner antibody occurs, and so postpones onset of the hook effect. The overall effect is to give a calibration curve covering a wider range of antigen concentrations but having a reduced slope, with the consequent disadvantage of a larger uncertainty in any determined antigen concentration.

WO-A-8911101 describes a more sophisticated assay technique which utilises high and low affinity binding partners respectively coated onto different types of monodisperse particles which are distinguishable by flow cytometry. Predetermined amounts of this binary particle mixture and of labelled ligand are incubated with the analyte, and the resulting two types of labelled ligand-carrying particles are thereafter independently but simultaneously detected by means of a flow cytometer, the analyte concentration being determined from the thus-obtained two measurement values by reference to a double standard calibration curve.

This dual affinity assay technique may be applied both to competitive binding assays, in which case the labelled ligand should have affinity for the binding partner, typically being a labelled version of the analyte, and to sandwich assays, in which case the labelled ligand should have affinity for the analyte. It is possible simultaneously to assay a plurality of analytes using a plurality of binary particle mixtures such that all the particle types are separately distinguishable by the flow cytometer.

The use of a double standard calibration curve enhances the precision of the assay and enables immediate detection of anomalous or incorrect results, since the two measurement values for a sample must fit as a pair to the double curve. Because the two types of particles are separately determined sensitivity at low concentrations, which is principally a function of the high affinity binding partner, is not compromised by the presence of the low affinity binding partner, which in turn permits high precision measurements at high analyte concentration and enhances the dynamic range of the assay by forestalling the hook effect. This may be contrasted with the immunoassay described in U.S. Pat. No. 4,595,661 which, when a labelled additional antibody is used, measures only the sum of the contributions from the two binding reactions, leading to reduced sensitivity at low antigen concentrations.

The present invention is based on the unexpected finding that a wide dynamic working range coupled with a high degree of precision may be achieved with a binary assay system, i.e. a system in which two independently determinable forms of binding partner are used and the analyte concentration is obtained from readings derived from these two forms by means of a double standard curve, if the two forms of binding partner have affinities for the analyte and labelled ligand respectively.

Thus according to one aspect of the present invention there is provided a method for assaying an analyte in a sample which comprises reacting the sample with a first binding partner having affinity for said analyte, a labelled ligand having affinity for said analyte or first binding partner, and a second binding partner having affinity for said labelled ligand, said first and second binding partners being in independently determinable solid-supported forms whereby signals in respect of the resulting labelled ligand-carrying first and second binding partners may be independently determined and the analyte concentration obtained therefrom by reference to a double standard calibration curve.

A number of different assay systems and detection techniques may be used in the method of the invention. Thus, for example, the first and second solid-supported binding partners may comprise binding partner-coated monodisperse particles of two types distinguishable by, for example, microscopic examination or photography on the basis of size or by flow cytometry on the basis of size or electrical impedance, e.g. as described in greater detail hereinafter. Alternatively the first solid-supported binding partner may, for example, be an appropriately coated dipstick or coated surfaces of the wells of a microtiter plate, with the second comprising appropriately coated microparticles or beads, these preferably being monodisperse, so that the two solid-supported forms may be separated and analysed after completion of the assay procedure, e.g. by spectroscopic, radiometric or photographic methods as appropriate. Other alternative systems include use of coated microparticles for the first binding partner and an appropriately coated filter for the second binding partner.

The sequence in which the various reagents and the analyte are combined may not be critical, although it will generally be desirable to incubate at least the analyate and labelled ligand in the first step of the procedure.

Thus, for example, it may be convenient initially to react the analyte and labelled ligand for a set period, thereafter adding the first and second binding partners either simultaneously or sequentially in either order. Alternatively one may initially combine e.g. the first binding partner and the labelled ligand with the sample, thereafter effecting reaction with the second binding partner. It may also be possible to combine the sample with all the reagents simultaneously. It will be appreciated that a standard sequence with predetermined incubation periods should preferably be used in any given assay system to enhance reproducibility of the results.

It will also be appreciated that the overall shape of the double standard calibration curve for a specific assay system within the ambit of the present invention will depend on whether a sandwich or competitive assay system is used. In the former case signals in respect of the labelled ligand-carrying second binding partner will decrease with increasing analyte concentration, as increasing amounts of labelled ligand are bound to the analyte, whereas in a competitive binding assay the amount of free labelled ligand available to react with the second binding partner will increase as the analyte concentration increases.

BRIEF DESCRIPTION OF THE DRAWINGS

In the accompanying drawing, which illustrates the invention without in any way limiting the same.

Figure 1:
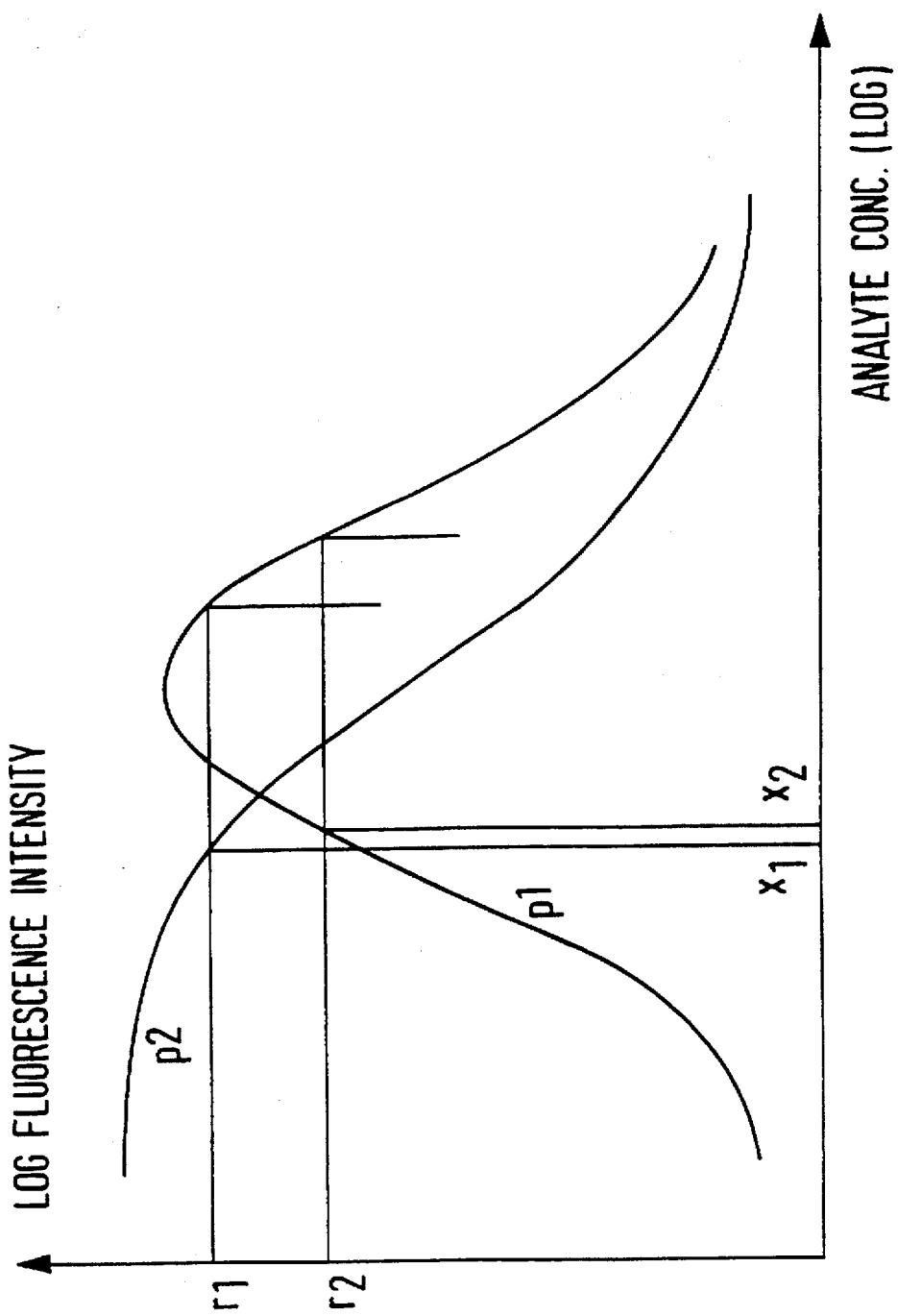
FIG. 1 illustrates a representative double standard curve comprising logarithmic plots of analyte concentration against fluorescence intensity for a sandwich assay system in which the labelled ligand comprises a fluorescent label having affinity for the analyte, the first and second binding partners comprise first and second particle types p1 and p2 having affinity for the analyte and labelled ligand respectively and being distinguishable e.g. by virtue of having different particle sizes, and detection is by means of flow cytometry.

It will be apparent from FIG. 1 that the standard curve for particle type p1 exhibits the usual hook effect, such that a specific fluorescence intensity cannot unambiguously be ascribed to a single analyte concentration value. When, however, such a p1 fluorescence intensity is measured in conjunction with a corresponding intensity for the p2 type particles, the combination of the two values is capable of providing an unambiguous determination of analyte concentration over a wide working range. Thus, in contrast to prior art procedures such as those described in U.S. Pat. No. 4,595,661 and U.S. Pat. No. 4,743,542, which endeavour to postpone or obviate the hook effect, the method of the invention makes practical use of the effect to extend its dynamic range.

As with the procedure of WO-A-8911101 the use of a double standard calibration curve permits ready detection of anomalous or incorrect results, since the two fluorescence intensity values for a particular sample must fit as a pair to the double curve. An unbiased estimate of an analyte concentration X may be obtained as a linear combination of the two concentrations $x_1$ and $x_2$ determined by observables $r_1$ and $r_2$ from each of the standard curves, taking into consideration that $r_1$ and r2 should fit the double standard curve as a pair. An improved estimate of the concentration may be determined from the relationship $X=ax_1 +(1-a)x_2$ where the value of a is determined by means of statistical theory such that the resulting variance of X is minimal.

Parameters such as levels of loading for and degrees of affinity exhibited by the first and second binding partners may be selected to ensure that, as shown in FIG. 1, the p2 curve exhibits a steep slope in the region where the p1 curve changes direction so that the p2 curve provides accuracy in the region where the p1 curve is subject to maximum variance.

The second binding partner in the method of the invention can in a sense be regarded as "washing away" unbound labelled ligand in a quantitatively determinable form from the analyte/first binding partner/labelled ligand system. This has the advantage that non-specific binding involving the labelled ligand may be reduced or even substantially completely eliminated, thereby minimising or removing a constraint on the sensitivity of the assay system at low analyte concentrations.

The method of the invention also has the advantage over that of WO-A-8911101 that it avoids the need to use pairs of binding partners having the same specificity but different affinity; it will be appreciated that for certain analytes such pairs may be difficult to obtain.

Where the first binding partner is in the form of coated particles these may conveniently carry a relatively high loading of the binding partner so as to maximise the amount of binding per particle and thereby enhance the sensitivity of the method at low analyte concentration.

The second binding partner is preferably used in excess relative to the labelled ligand in order to ensure rapid binding of residual unbound labelled ligand. The use of a substantial excess of the second binding partner may tend to enhance the speed at which this binding occurs and may therefore be particularly preferred where shorter overall assay times (e.g. 1 to 2 hours) are desired. The level of loading of the second binding partner on its solid support system is not critical and may be chosen to suit a particular assay system.

Incubation times used for the method of the invention are not critical, although as has previously been noted they should desirably be standardised for a particular system in the interests of reproducibility. Where a series of sequential reaction steps are performed individual incubation times in the range 5 minutes to 2 hours per step may for example be used.

Embodiments of the method of the invention which employ distinguishable particle types may if desired be used for the simultaneous sandwich assay of a plurality of analytes. A, A', A" . . . etc. by using an appropriate number of labelled ligands L, L', L" . . . etc. each having specific affinity for its target analyte, sets of first particle types p1, p1', p1" . . . etc. carrying first binding partners each having specific affinity for its target analyte, and sets of second particle types p2, p2', p2" . . . etc. carrying second binding partners each having specific affinity for the corresponding labelled ligand, provided that all the individual particle types p1, p1', p1" . . . , p2, p2', p2". . . etc. are separately distinguishable, e.g. by flow cytometry. Reference may then be made to an appropriate number of double standard calibration curves for the various p1/p2, p1'/p2', p1"/p2" . . . etc. particle pair combinations.

In embodiments of the method of the invention employing distinguishable particle types, the second binding partner may if desired be coupled to two distinguishable types of particle, the first type preferably carrying a relatively high loading of the second binding partner and being used in relatively small amount in order to achieve maximum sensitivity, and the second type subsequently being added in excess (e.g. after 1 hour) to promote rapid establishment of equilibrium. Signals obtained in respect of the p1 particles and the two types of p2 particles may then be referred to a triple standard curve, permitting the analyte concentration to be determined with even greater precision than is afforded by a double standard curve.

Alternatively in this embodiment the two types of second binding partner may comprise two different forms of binding partner, one binding the labelled ligand at the analyte-specific site and the other binding outside this site so that it will bind labelled ligand irrespective of its binding to analyte.

In general in assays according to the invention which use flow cytometric detection, the various particle types are conveniently distinguished by size, since conventional flow cytometers can determine particle size on the basis of the amount of light scattered by the particles. A wide range of types of monosized particles having different compositions, diameters, reactive surface groups etc. are commercially available, e.g. from Dyno Particles, Lillestrøm, Norway, and appropriate sets of such particles may be used in accordance with the invention. Since such particles are highly monosized, e.g. exhibiting a relative standard deviation not exceeding 1% in light scatter measurements for a sample population, a substantial number of such particle types may be mixed and easily identified as non-overlapping populations in a flow cytometric light scatter histogram.

Use may alternatively or additionally be made of the Coulter principle whereby particles are distinguished by differences in electrical impedance resulting from differences in particle size.

As noted above, it will be necessary when a plurality of analytes is to be assayed simultaneously that all the individual particle types are separately distinguishable, e.g. by flow cytometry. Thus if the various labelled ligand of different specificities all contain the same label component it will be necessary for every individual particle type of the various pairs p1/p2, p1'/p2', p1"/p2" . . . etc. to be distinguishable from the other particle types by a detectable particle characteristic. If, on the other hand, differently labelled ligands specific for each analyte are used, this will permit the various pairs of particle types to be distinguished from each other in terms of qualitative differences in the signals from the labels, e.g. the wavelength of fluorescence signals, so that identically sized particles may if desired be used for all the p1, p1', p1"... etc. particle types, a different set of identically sized particles being used for all the p2, p2', p2"... etc. particle types.

Preferred labels for use in the method of the invention include fluorescent substances such as are commonly used in fluorometric flow cytometry, for example fluorescein or phycoerythrin, or fluorochromes for delayed, time-resolved fluorescence. Such labels may if desired be in the form of fluorescently-stained microspheres, e.g. having diameters of 0.10 microns, for example as described by Saunders et al. in Clin. Chem. 31, 2020. Other labels providing a photometric signal include metal-based systems such as sols of colloidal gold particles. Labels capable of providing significant differences in electrical impedance, for example metal (e.g. gold) particles, may also be used to provide signals which may be detected by the Coulter principle, differences in particle type then being determined by size-dependent properties such as light scattering.

As has previously been noted the labelled ligand, which is normally employed in a predetermined amount, should be such as to have affinity for the binding partner in the case of a competitive binding assay or for the analyte in the case of a sandwich assay. In the latter type of procedure, which represents a preferred feature of the invention, the labelled ligand and binding partner preferably attach to different binding sites (e.g. epitopes) on the analyte; for convenience the analyte may be regarded as having binding sites a for which the binding partner is specific and binding sites b for which the labelled ligand is specific.

In sandwich assays according to the process of the invention the second binding partner may conveniently comprise a solid-supported form of the analyte, since this will have the necessary affinity for the labelled ligand. It may for example be convenient initially to coat the solid support with first binding partner and then to couple analyte thereto, if desired using a fixative or other crosslinking agent to strengthen the binding; in this way the b binding sites of the analyte are left free to react with the labelled ligand.

Alternatively the second binding partner in a sandwich immunoassay system may be an anti-idiotypic antibody which mimics the binding site for which the labelled ligand has affinity.

In competitive assays, where the labelled ligand has affinity for the first binding partner, the second binding partner may, for example, comprise a solid-supported form of a material having affinity for the label part of the labelled ligand. An example of such a material would be an anti-FITC antibody.

Coating of solid support systems for use in the method of the invention can be effected using, for example, procedures standard in the art. Thus, for example, representative techniques for coating monosized particle systems with antibodies for use in immunoassay procedures are described by Frengen et al. in Clin. Chem. 39 (1993), pp. 2174–2181 and the references contained therein, and by Lindmo et al. in J. Immunol. Meth. 126 (1990), pp. 183–189.

The method of the invention may be used to assay a wide range of analytes, the only limiting requirement for a particular analyte being the existence of a specific binding partner therefor which is capable of being coupled to the surfaces of an appropriate solid support system. Analyte and binding partner pairs may, for example, be selected from any of the following combinations, in which either member of the pair may be the analyte and the other the binding partner:

(a) antigen and specific antibody;
(b) hormone and hormone receptor;
(c) hapten and antihapten;
(d) polynucleotide and complementary polynucleotide;
(e) polynucleotide and polynucleotide binding protein;
(f) biotin and avidin or streptavidin;
(g) enzyme and enzyme cofactor; and
(h) lectin and specific carbohydrate.

A member from one of the above pairs, e.g. biotin or a hapten, may if desired be attached to some other molecule and the resulting "secondary" analyte may then be assayed in order to determine indirectly the concentration of the "primary" molecule.

Antigens are one category of preferred analytes for use in the method of the invention, the preferred binding partners therefor being monoclonal antibodies.

According to a further feature of the invention there is provided a kit for use in the assay of an analyte in a sample comprising:

(i) a first solid support system carrying or being adapted to carry a first binding partner having affinity for the analyze;
(ii) a labelled ligand having affinity for the analyte or said first binding partner; and
(iii) a second solid support system carrying or being adapted to carry a second binding partner having affinity for said labelled ligand;

the two forms of solid support systems being such that the amounts of labelled ligand becoming bound to each form in an assay procedure may be independently determined.

The two forms of solid support system advantageously comprise sets of monodisperse particles, e.g. having different sizes which may therefore be distinguished by techniques such as flow cytometry. Such particles may be coated with selected binding partners or may possess absorption sites or reactive groups on their surfaces in order to permit absorption of or coupling to a binding partner of choice.

The kits of the invention may if desired contain a plurality of pairs of solid support systems, preferably different types of monodisperse particles, in order to permit the simultaneous assay of a plurality of analyzes in a sample.

The following non-limitative Example serves to illustrate the invention.

EXAMPLE

The test analyte was intact human Chorionic Gonadotropin (hCG) obtained from Calbiochem (La Jolla, Calif.-Can. No. 869031). A series of standards of known concentration were prepared therefrom by serial dilution with assay buffer (vide infra).

The two forms of solid-supported binding partners comprised macroporous acrylate particles with surface epoxy groups and having diameters of 6.5 and 7.5 µm respectively, developed by SINTEF, Trondheim, Norway and hereinafter respectively referred to as MP 6.5 and MP 7.5. MP 6.5 was coated with a mouse monoclonal antibody E26 established at the Norwegian Radium Hospital and having affinity for an epitope of the α-subunit of hCG in similar manner to that described by Frengen et al. in Clin. Chem. 39 (1993), pp. 2174–2181, using 150 µg E26/mg particles. MP 7.5 was coated in a similar manner with purified hCG β-subunit obtained from Calbiochem (Cat. No. 969126) using 30 µg hCG β-subnit/mg particles.

The labelled ligand was prepared from a mouse monocional antibody E27 established at the Norwegian Radium Hospital and having affinity for an epitope of the β-subunit of hCG. This was reacted with biotin using a molar ratio of biotin to antibody of 10:1, and the resulting biotinylated E26 (at a concentration of 1.9 mg/l) was mixed with streptavidin-R-phycoerythrin (Becton Dickinson) in a ratio of 6:1 v/v.

The assay buffer used in the procedure was phosphate buffered saline containing 10 g bovine serum albumin, 1 g sodium azide and 1 ml Tween 20 per liter.

In each of a series of assay reagent tubes, 20 μl of labelled antibody and 50 μk of assay buffer were mixed with a 10 μl hCG sample in assay buffer. After a minimum 15 minutes of incubation, 20 μl of a suspension in assay buffer of particles MP 6.5 and MP 7.5, both at a concentration of 310 mg/l, were added. The mixture was incubated for 1–1.5 hours on a horizontal rotational shaker at room temperature whereafter small volumes of the contents of each tube were measured by a flow cytometer, without prior washing. For comparison identical assays excluding the MP 7.5 particles were also performed.

Flow cytometric fluorescence and light scatter measurements were performed using a Skatron Argus Flow Cytometer equipped with a 75 watt mercury-xenon lamp. The filterblock used provided excitation in the wavelength range 510–560 nm and fluorescence measurements in the range 590–640 nm. Particle-associated light scatter and fluorescence signals were measured simultaneously and registered as correlated two-parameter histograms. By gating on appropriate windows in the light scatter histogram, fluorescence intensity from the different particles of interest was obtained. The median channel of the logarithmic fluorescence histogram was taken as a measure for the particle-associated fluorescence.

Figure 2A:
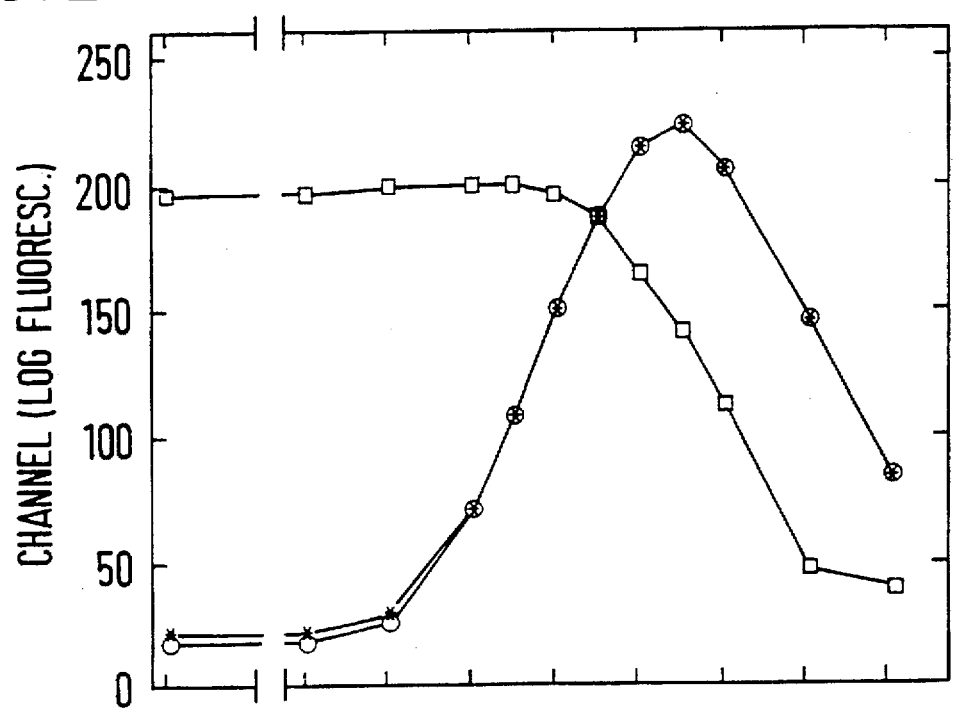
FIG. 2A represents such a double standard curve obtained experimentally as described in the Example.

The simultaneously-measured standard curves for MP 6.5 particles and MP 7.5 particles are shown in FIG. 2A of the accompanying drawings by circles and squares respectively. The standard curve for the assay results with only MP 6.5 particles present is indicated by asterisks.

The results show that the standard curves for the MP 6.5 particles in the two experiments overlap closely, except for a small divergence at low analyte concentration resulting from slightly reduced non-specific binding when the MP 7.5 particles were included.

Figure 2B:
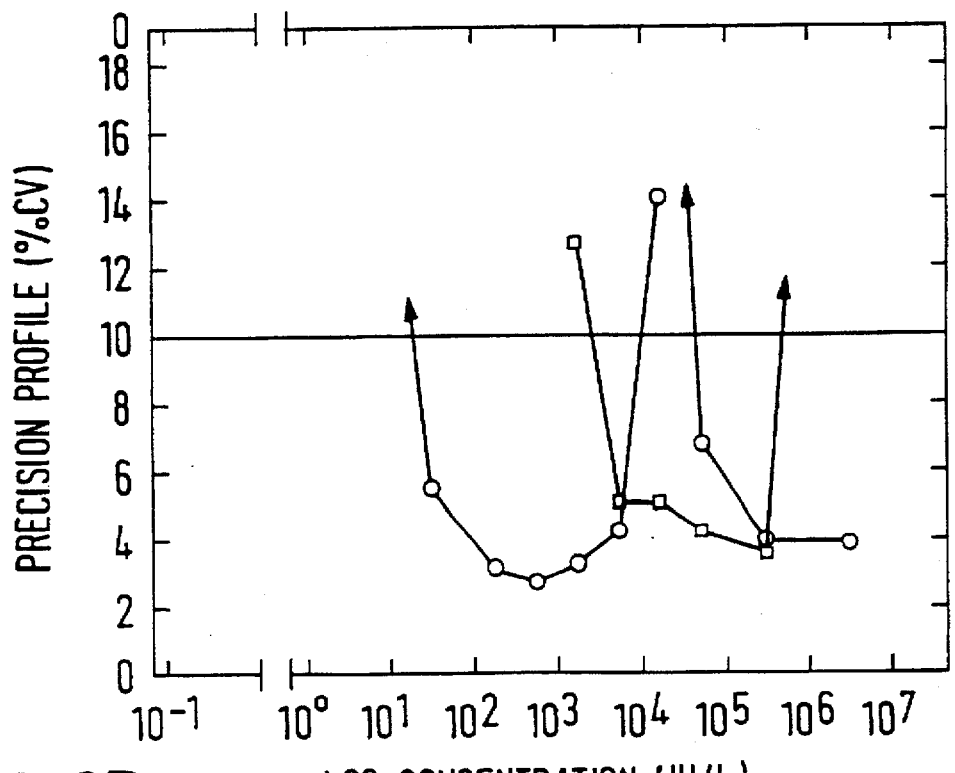
FIG. 2B represents the double precision profile for the two curves.

The precision profiles for the MP 6.5 and MP 7.5 particles as shown in FIG. 2B are expressed in terms of the coefficient of variance (CV):

$$CV = \sigma_{R_i} * [\delta(lnD)/\delta R_i] * 100 \, [\%]$$

where $R_i$ is the measured response of particle (i) expressed as channel number of logarithmic fluorescence intensity, $\sigma_{R_i}$ is the corresponding standard deviation in $R_i$, estimated to be 1 channel in the present experiment, and D denotes the dose (i.e. concentration of hCG).

The precision profiles for the MP 6.5 and MP 7.5 particles show that either one or both standard curves provide a CV<10% throughout the concentration range ~20–>3×10$^6$ IU/l hCG. The ambiguity in the standard curve for MP 6.5 particles whereby the same response may be obtained for a high and a low hCG concentration is eliminated by the additional information obtained from the MP 7.5 particles, which in the illustrated sandwich assay embodiment have a standard curve with monotonous decreasing slope.

I claim:

1. A method for assaying an analyte in a sample which comprises
   (a) reacting the sample with:
      (i) a first binding partner having affinity for said analyte; and either
      (ii)(a) a labelled ligand having affinity for said analyte, and
      (iii)(a) a second binding partner having affinity for said labelled ligand; or
      (ii)(b) a labelled ligand comprising a labelled form of said analyte, and
      (iii)(b) a second binding partner having affinity for the label of said labelled ligand;

wherein said first and second binding partners are respectively immobilized on a first and second independently determinable solid support; and (b) independently determining labelled ligand-carrying first and second solid supports and obtaining analyte concentration therefrom by reference to a double standard calibration curve.

2. The method as claimed in claim 1 wherein the first and second solid supports comprise two distinguishable sets of monosized particles.

3. The method as claimed in claim 2 wherein said two sets of monosized particles are distinguishable on the basis of size.

4. The method as claimed in claim 2 wherein said two sets of monosized particles are determined by flow cytometry.

5. The method as claimed in claim 1 wherein the second binding partner is used in excess relative to the labelled ligand.

6. The method as claimed in claim 2 wherein a plurality of analytes is simultaneously assayed using an appropriate number of labelled ligands and pairs of immobilized first and second binding partners.

7. The method as claimed in claim 1 wherein the ligand is labelled with a fluorescent substance.

8. The method as claimed in claim 1, wherein the analyte is an antigen and the first and second binding partners are monoclonal antibodies.

9. A method for assaying an analyte in a sample which comprises:
   (a) reacting the sample with:
      (i) a first binding partner having affinity for said analyte; and either
      (ii)(a) a labelled ligand having affinity for said analyte, and
      (iii)(a) a second binding partner having affinity for said labelled ligand;
      (ii)(b) a labelled ligand comprising a labelled form of said analyte, and
      (iii)(b) a second binding partner having affinity for the label of said labelled ligand;

wherein said first binding partner is immobilized on a first set of monosized particles and said second binding partner is immobilized on a combination of a second and third set of monosized particles, said first, second, and third sets of monosized particles being independently determinable; and (b) independently determining labelled ligand-carrying first, second, and third monosized particles and obtaining analyte concentration therefrom by reference to a triple standard calibration curve.

10. A kit for use in the assay of at least one analyte in a sample, said kit comprising:

(i) a first binding partner having affinity for said analyte; and either (ii)(a) a labelled ligand having affinity for said analyte, and (iii)(a) a second binding partner having affinity for said labelled ligand;

or (ii)(b) a labelled ligand comprising a labelled form of said analyte, and (iii)(b) a second binding partner having affinity for the label of said labelled ligand;

wherein said first and second binding partners are respectively immobilized on a first and second independently determinable solid support.

11. The kit as claimed in claim 10 wherein the first and second solid supports comprise two sets of distinguishable monosized particles.

12. The kit as claimed in claim 11 wherein said two sets of monosized particles are distinguishable by size.

13. The kit as claimed in claim 10 for use in the assay of multiple analytes in a sample, said kit comprising an appropriate number of labelled ligands and pairs of immobilized first and second binding partners.

14. The kit as claimed in claim 10 wherein the second independently determinable solid support comprises a combination of two distinguishable sets of monosized particles.

* * * * *